United States Patent
Doran et al.

(10) Patent No.: US 10,820,824 B2
(45) Date of Patent: Nov. 3, 2020

(54) COMBINED STIMULATOR AND BIPOLAR ELECTRODE ASSEMBLY FOR MOUSE ELECTRORETINOGRAPHY (ERG)

(71) Applicant: Diagnosys LLC, Lowell, MA (US)

(72) Inventors: Bruce Doran, Lowell, MA (US); Marc Chabot, Lowell, MA (US)

(73) Assignee: Diagnosys LLC, Lowell, MA (US)

( * ) Notice: Subject to any disclaimer, the term of this patent is extended or adjusted under 35 U.S.C. 154(b) by 841 days.

(21) Appl. No.: 15/153,286

(22) Filed: May 12, 2016

(65) Prior Publication Data

US 2017/0042441 A1     Feb. 16, 2017

Related U.S. Application Data

(60) Provisional application No. 62/160,503, filed on May 12, 2015.

(51) Int. Cl.
*A61B 5/0496* (2006.01)
*A61B 3/00* (2006.01)
(Continued)

(52) U.S. Cl.
CPC .......... *A61B 5/0496* (2013.01); *A61B 3/0008* (2013.01); *A61B 5/6821* (2013.01);
(Continued)

(58) Field of Classification Search
CPC ... A61B 5/0496; A61B 5/6821; A61B 3/0008; A61B 2090/306; A61B 2503/40;
(Continued)

(56) References Cited

U.S. PATENT DOCUMENTS

| 3,012,472 A | | 12/1961 | Feinberg et al. | |
| 3,439,157 A | * | 4/1969 | Myles | F21K 2/00 362/551 |

(Continued)

FOREIGN PATENT DOCUMENTS

| CN | 101019760 | 8/2017 |
| EP | 0225072 | 6/1987 |

(Continued)

OTHER PUBLICATIONS

Burr-Brown Products From Texas Instruments, Single-Supply Differential Amplifier, Texas Instruments Incorporated, 2001.

(Continued)

*Primary Examiner* — Linda C Dvorak
*Assistant Examiner* — Annabeth E Rodriguez
(74) *Attorney, Agent, or Firm* — Pandiscio & Pandisciso

(57) ABSTRACT

Apparatus for evoking and sensing ophthalmic physiological signals in an eye, the apparatus comprising: an elongated tubular light pipe having a longitudinal axis, a distal end and a proximal end, the distal end terminating in a spheroid recess; an active electrode having a distal end and a proximal end, the active electrode being mounted to the elongated tubular light pipe and extending proximally along the elongated tubular light pipe so that the distal end of the active electrode terminates at the spheroid recess at the distal end of the elongated tubular light pipe; and a reference electrode having a distal end and a proximal end, the reference electrode being mounted to the elongated tubular light pipe and extending proximally along the elongated tubular light pipe so that the distal end of the reference electrode terminates at the spheroid recess at the distal end of the elongated tubular light pipe; wherein the distal end of the active electrode is located closer to the longitudinal axis of the (Continued)

elongated tubular light pipe than the distal end of the reference electrode.

31 Claims, 17 Drawing Sheets

(51) Int. Cl.
    *A61B 5/00*     (2006.01)
    *A61B 90/30*     (2016.01)

(52) U.S. Cl.
    CPC ..... *A61B 2090/306* (2016.02); *A61B 2503/40* (2013.01); *A61B 2503/42* (2013.01); *A61B 2562/0209* (2013.01); *A61B 2562/182* (2013.01)

(58) Field of Classification Search
    CPC ........ A61B 2503/42; A61B 2562/0209; A61B 2562/182
    See application file for complete search history.

(56) References Cited

U.S. PATENT DOCUMENTS

| | | | |
|---|---|---|---|
| 4,131,113 A * | 12/1978 | Fender | A61B 5/0496 351/212 |
| 4,362,164 A | 12/1982 | Little et al. | |
| 4,618,230 A | 10/1986 | Ens et al. | |
| 4,740,072 A | 4/1988 | Griffin et al. | |
| 4,806,289 A | 2/1989 | Laursen et al. | |
| 4,874,237 A * | 10/1989 | Cringle | A61B 5/0496 221/221 |
| 4,910,090 A * | 3/1990 | Kuhlman | H01J 29/868 174/390 |
| 5,141,305 A | 8/1992 | Young | |
| 5,943,116 A | 8/1999 | Zeimer | |
| 6,231,187 B1 | 5/2001 | Munoz | |
| 8,810,482 B2 | 8/2014 | Abdollahi et al. | |
| 2003/0020875 A1 | 1/2003 | Sperling | |
| 2003/0149350 A1 | 8/2003 | Porciatti | |
| 2006/0058857 A1 | 3/2006 | Tano et al. | |
| 2006/0244915 A1 | 11/2006 | Clemons et al. | |
| 2008/0294066 A1 | 11/2008 | Hetling et al. | |
| 2010/0091242 A1 | 4/2010 | Baglini et al. | |
| 2010/0249532 A1 | 9/2010 | Maddess et al. | |
| 2010/0292999 A1 | 11/2010 | Verma | |
| 2011/0170064 A1 | 7/2011 | Taylor | |
| 2012/0069296 A1 | 3/2012 | Li et al. | |
| 2013/0242077 A1 | 9/2013 | Lin et al. | |
| 2013/0278899 A1 | 10/2013 | Waldorf et al. | |
| 2013/0285886 A1 | 10/2013 | Pombo et al. | |
| 2014/0128763 A1 | 5/2014 | Fadem | |
| 2015/0029463 A1* | 1/2015 | Hetling | A61B 5/6821 351/219 |
| 2015/0313467 A1 | 11/2015 | Sakai et al. | |
| 2017/0014074 A1 | 1/2017 | Etzkorn et al. | |
| 2017/0042441 A1 | 2/2017 | Doran et al. | |
| 2017/0127970 A1 | 5/2017 | Doran et al. | |

FOREIGN PATENT DOCUMENTS

| | | |
|---|---|---|
| EP | 2314201 | 4/2011 |
| WO | WO 2015/191240 | 12/2015 |
| WO | WO 2016/162796 | 10/2016 |

OTHER PUBLICATIONS

Heath, Janet, Amplifiers: What do rail-to-rail and single supply mean?, Analog IC Tips, 2017, https://www.analogictips.com/amplifiers-rail-to-rail-single-supply-mean/.

Matsumoto, Celso S. et al., Pattern Visual Evoked Potentials Elicited by Organic Electroluminescence Screen, BioMed Research International, vol. 2014, pp. 1-6.

Luo, Xunda et al. Retinal Pathway Origins of the Pattern Electroretinogram (PERG), Investigative Ophthalmology & Visual Science, vol. 52, No. 12, Nov. 2011, pp. 8571-8584.

Viswanathan, Suresh et al. The Uniform Field and Pattern ERG in Macaques With Experimental Glaucoma: Removal of Spiking Activity, Investigative Ophthalmology & Visual Science, vol. 41, No. 9, Aug. 2000, pp. 2797-2810.

* cited by examiner

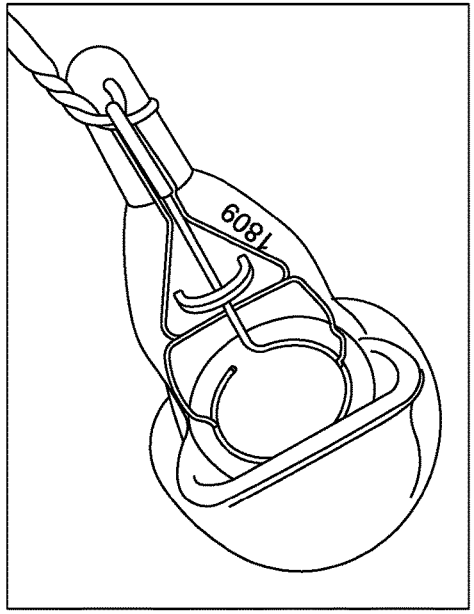
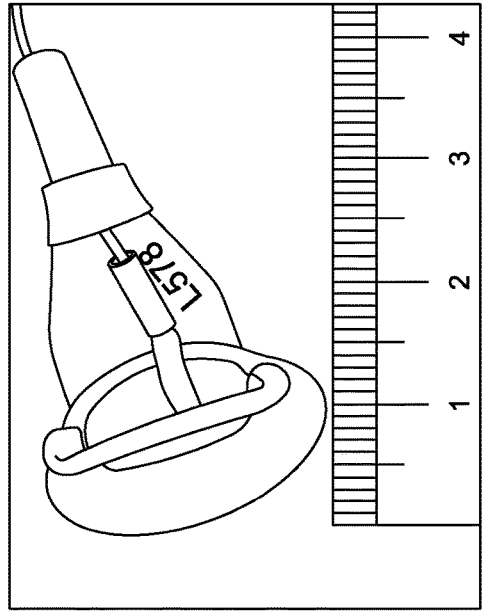
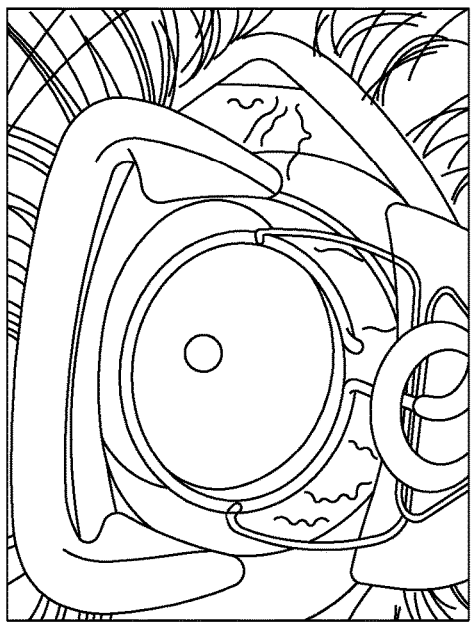
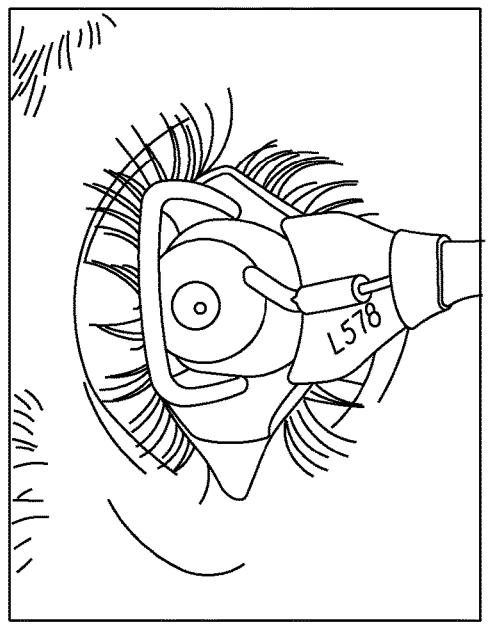
Burian speculum type electrodes
Cotton wick electrodes
FIG. 4
(PRIOR ART)

Mouse ERG electrode

COMBINED STIMULATOR AND BIPOLAR ELECTRODE ASSEMBLY FOR MOUSE ELECTRORETINOGRAPHY (ERG)

REFERENCE TO PENDING PRIOR PATENT APPLICATION

This patent application claims benefit of prior U.S. Provisional Patent Application Ser. No. 62/160,503, filed May 12, 2015 by Diagnosys LLC and Bruce Doran et al. for COMBINED STIMULATOR AND BIPOLAR ELECTRODE ASSEMBLY FOR MOUSE ELECTRORETINOGRAPHY (ERG), which patent application is hereby incorporated herein by reference.

FIELD OF THE INVENTION

This invention relates generally to apparatus and methods for the assessment of electrophysiological signals, and more particularly to apparatus and methods for the assessment of ophthalmic physiological signals.

BACKGROUND OF THE INVENTION

Full-field ophthalmic electrophysiology generally involves flashing a light from a large "bowl" into the eye of the subject, and then measuring the response from the retina of the subject using electrodes, i.e., an active electrode which contacts the eye of the subject and other electrodes (reference and ground electrodes) which contact other portions of the subject. This procedure is sometimes referred to as electroretinography (ERG).

Clinically, the hardest part of performing ophthalmic electrophysiology is properly connecting the electrodes to the subject and, more particularly, properly connecting the active electrode to the eye of the subject.

In some cases the ophthalmic electrophysiology must be conducted on humans. In other cases the ophthalmic electrophysiology must be conducted on small rodents of the sort commonly used in laboratory experiments, e.g., mice and rats (for the purposes of the present invention, such animals will generally be referred to herein as "mice", however, it should be appreciated that such term is meant to be exemplary and not limiting). It will be appreciated that conducting electrophysiology on mice can present issues which may be different from the issues which might arise when conducting electrophysiology on humans.

In present configurations for performing ophthalmic electrophysiology on mice, e.g., with an ERG dome such as that offered by Diagnosys LLC of Lowell, Mass., the anesthetized mouse is placed on a heated platform that maintains its body temperature during the test. At least three electrodes must be attached to the mouse: (i) a ground electrode; (ii) a reference electrode; and (iii) a corneal (active) electrode. In best current practice, all three electrodes are made out of platinum or silver/silver chloride and consist of two needles and a wire. One of the needles is used as a ground electrode and is easy to attach to the mouse because its position is not critical—anywhere in the haunch or tail of the mouse will do. Placement of the other two electrodes (i.e., the reference and active electrodes) requires much more care. The remaining needle electrode is the reference electrode. It must be inserted very precisely into the mouse, either at the midline of the scalp, in the mouth, or in the cheek. Mispositioning of the reference electrode will cause imbalances in the readings between the two eyes of the mouse. The last electrode, the wire electrode, is the corneal (active) electrode. It too must be placed in just the right position on the eye in order to avoid biasing the recording: too close to the center of the eye and the wire will block light; too far to the periphery of the eye and the wire will record lower voltages than if placed nearer to the center of the eye. If both eyes of the animal are to be tested, a second corneal wire must be placed in a homologous position to the first corneal wire. An added complication is that, usually, all this must be done in a room only dimly illuminated by deep red light.

After the three electrodes have been placed on the mouse, the ERG dome is either moved into position over the mouse or the platform supporting the mouse is moved into the dome. Either movement may disturb the electrodes placed on the mouse, which would then require that the electrodes be repositioned. Since the mouse is hidden by the dome, it sometimes wakes up and escapes under cover of darkness.

FIG. 1 shows the current Diagnosys mouse ERG dome platform in its open position.

FIG. 2 shows the same Diagnosys mouse ERG dome platform in its closed position.

It will be appreciated that conducting ophthalmic electrophysiology on a mouse is time-consuming and requires personnel with special skills. For this reason, ophthalmic electrophysiology is sometimes not performed on mice even where the results of performing ophthalmic electrophysiology could be beneficial. By way of example but not limitation, NIH has an impending campaign to phenotype more than 300,000 mutated mice. Among other things, the mice are being tested for deficits analogous to human eye disease. Although some of these deficits can only be detected using ophthalmic electrophysiology, electrophysiology was initially excluded from the testing protocols because existing techniques for performing ophthalmic electrophysiology on mice are too time-consuming and require personnel with rare skills.

Ophthalmic electrophysiology would be significantly easier to perform on mice if there were a way to rapidly and automatically position the active and reference electrodes on the mouse. There is an existing device (a "contact lens bipolar corneal electrode") that does this effectively for humans, but in its present state the contact lens bipolar corneal electrode is not practical for widespread use with mice.

More particularly, a contact lens bipolar corneal electrode consists of a lid-retracting speculum with a reference electrode embedded in its outer circumference. A contact lens ringed by the corneal electrode is suspended by a spring from the inner part of the speculum. Since both active and reference electrodes are built into the device, the two electrodes occupy the same position on every eye (which is easily adjusted during manufacture to be at the correct position on the eye of the subject). As a result, the contact lens bipolar corneal electrode provides highly reliable positioning of the active and reference electrodes, and hence provides highly reliable results. A further advantage of the contact lens bipolar corneal electrode is that both electrodes (active and reference) touch the tear film, making excellent electrical contact with the subject without special preparation.

FIG. 3 shows a human contact lens bipolar corneal electrode which was introduced by Diagnosys in 1986.

FIG. 4 shows another human contact lens bipolar corneal electrode sold by Hansen Ophthalmic Development Laboratories of Coralville, Iowa (hereinafter "Hansen Labs").

As noted above, human contact lens bipolar corneal electrodes work effectively, but mouse contact lens bipolar corneal electrodes are impractical for widespread use with mice. More particularly, a mouse contact lens bipolar corneal electrode is available from Hansen Labs, but the mouse contact lens bipolar corneal electrode is impractically delicate, expensive, and hard to make. The basic problem with the mouse contact lens bipolar corneal electrode sold by Hansen Labs is that the manufacturer does not know how its customers are going to use the lens—they may have an application that needs the animal to view an image—and so the manufacturer has to start by wrapping a corneal electrode around an optically "good", zero-power mouse contact lens, and this is a challenging task.

Another problem with mouse contact lens bipolar corneal electrodes is that, if anything, they slow the testing process down rather than speed it up. The mouse contact lens bipolar corneal electrodes are so delicate and sensitive that they require great care and skill in order to place them properly on the eye of the mouse—by way of example but not limitation, it is very easy to accidentally cover the mouse contact lens bipolar corneal electrodes with saline solution which shorts them out, and they often break during handling. In any case, mouse contact lens bipolar corneal electrodes are so hard to make that they are usually now offered only in monopolar versions, which means that the problem of placing the reference electrode on the mouse is still left to the user. The only real advantage of current mouse contact lens bipolar corneal electrodes over current wire electrodes is that the mouse contact lens bipolar corneal electrodes cover the cornea and prevent the formation of cataracts in the mouse due to drying.

FIG. 5 shows the mouse contact lens bipolar corneal electrode sold by Hansen Labs.

Thus there is a need for a new and improved approach for quickly and easily performing ophthalmic electrophysiology on mice.

SUMMARY OF THE INVENTION

The present invention comprises the provision and use of a new and improved method and apparatus for quickly and easily performing ophthalmic electrophysiology on mice.

In one form of the present invention, there is provided apparatus for evoking and sensing ophthalmic physiological signals in an eye, the apparatus comprising:

an elongated tubular light pipe having a longitudinal axis, a distal end and a proximal end, the distal end terminating in a spheroid recess;

an active electrode having a distal end and a proximal end, the active electrode being mounted to the elongated tubular light pipe and extending proximally along the elongated tubular light pipe so that the distal end of the active electrode terminates at the spheroid recess at the distal end of the elongated tubular light pipe; and a reference electrode having a distal end and a proximal end, the reference electrode being mounted to the elongated tubular light pipe and extending proximally along the elongated tubular light pipe so that the distal end of the reference electrode terminates at the spheroid recess at the distal end of the elongated tubular light pipe;

wherein the distal end of the active electrode is located closer to the longitudinal axis of the elongated tubular light pipe than the distal end of the reference electrode.

In another form of the present invention, there is provided a method for evoking and sensing ophthalmic physiological signals in an eye, the method comprising:

providing apparatus comprising:

an elongated tubular light pipe having a longitudinal axis, a distal end and a proximal end, the distal end terminating in a spheroid recess;

an active electrode having a distal end and a proximal end, the active electrode being mounted to the elongated tubular light pipe and extending proximally along the elongated tubular light pipe so that the distal end of the active electrode terminates at the spheroid recess at the distal end of the elongated tubular light pipe; and a reference electrode having a distal end and a proximal end, the reference electrode being mounted to the elongated tubular light pipe and extending proximally along the elongated tubular light pipe so that the distal end of the reference electrode terminates at the spheroid recess at the distal end of the elongated tubular light pipe;

wherein the distal end of the active electrode is located closer to the longitudinal axis of the elongated tubular light pipe than the distal end of the reference electrode;

positioning the elongated tubular light pipe against the eye of a test subject; and introducing light into the proximal end of the elongated tubular light pipe.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIG. 4 are schematic views showing prior art Burian speculum type electrodes and prior art cotton wick electrodes;

DETAILED DESCRIPTION OF THE PREFERRED EMBODIMENTS

Figure 1:
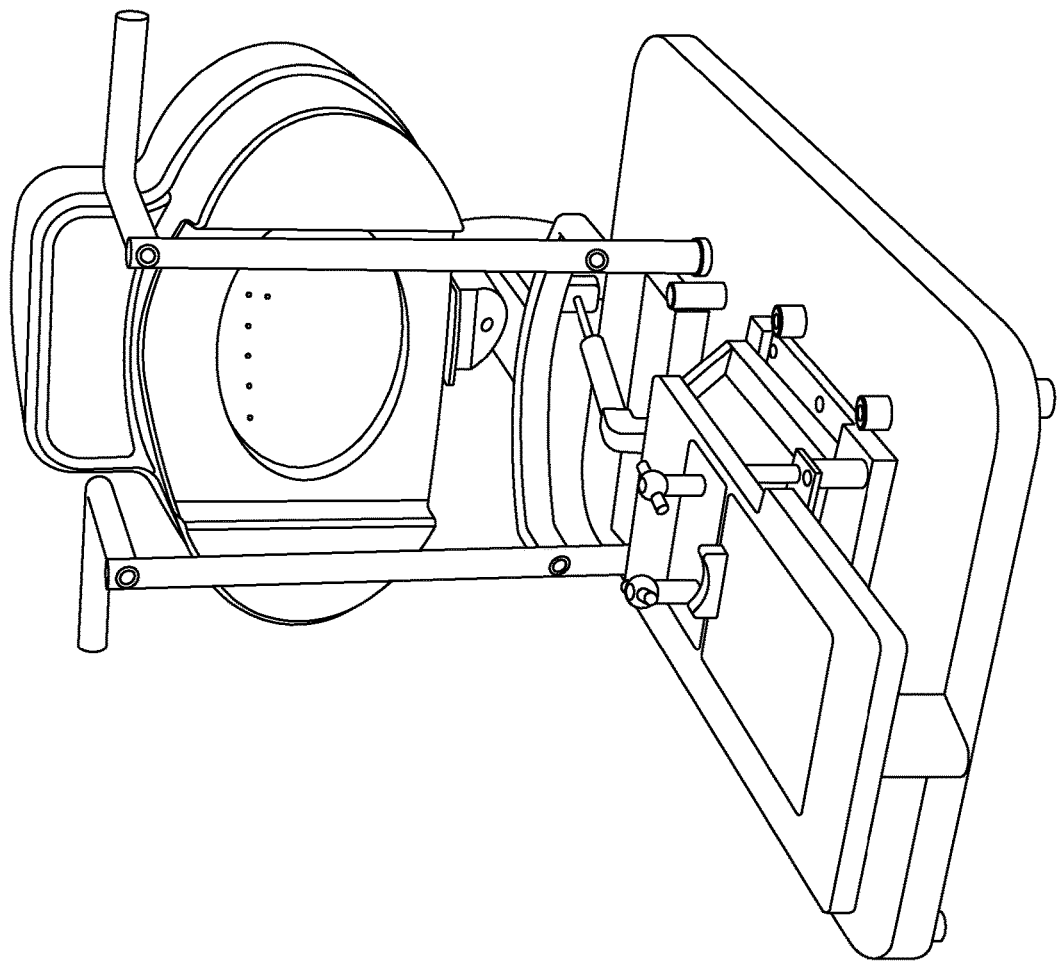
FIGS. 1 and 2 are schematic views of a prior art rodent table for the ColorDome Stimulator of Diagnosys LLC.
Figure 2:
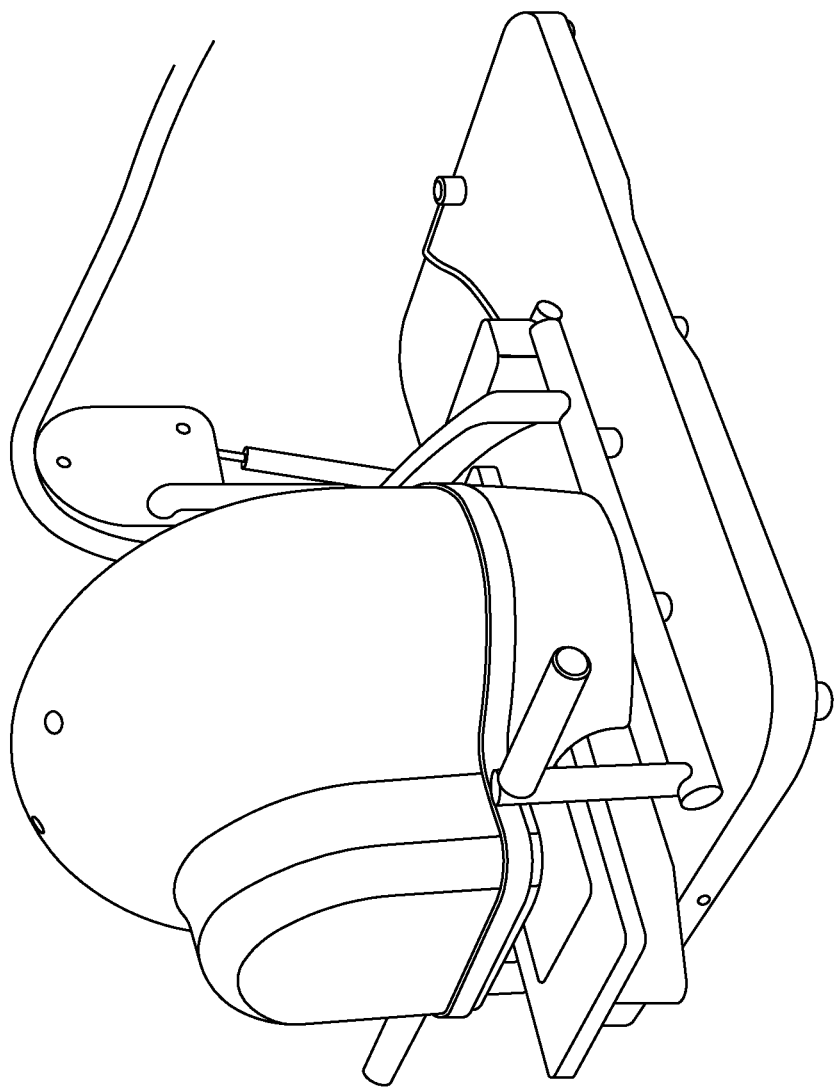
Figure 3:
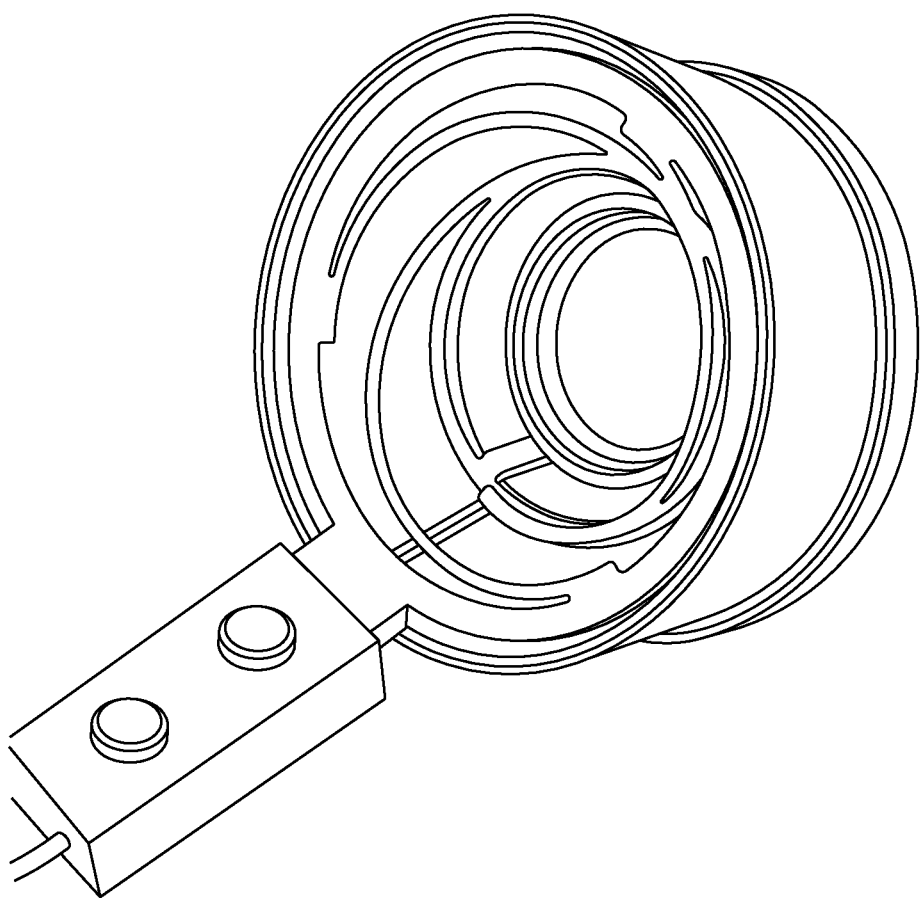
FIG. 3 is a schematic view of a prior art GoldLens Corneal Electrode.
Figure 5:
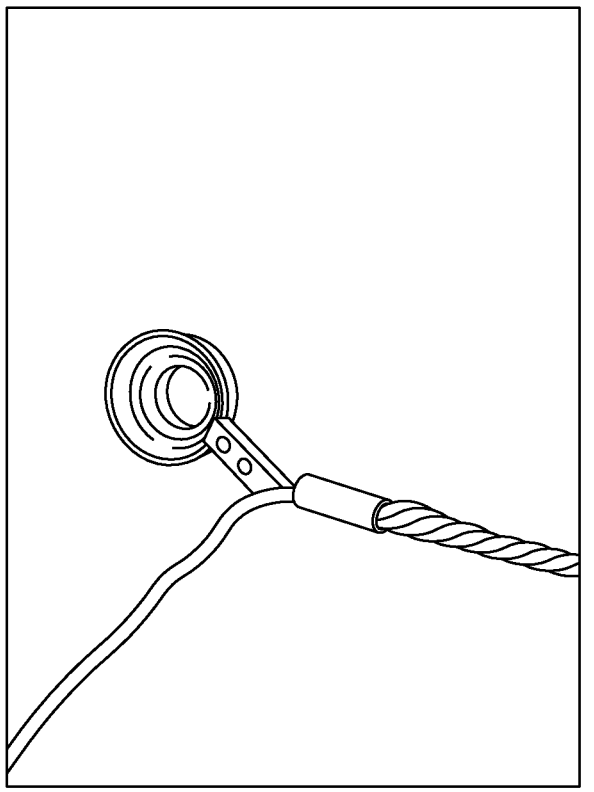
FIG. 5 is a schematic view showing a prior art mouse ERG electrode.
Figure 6:
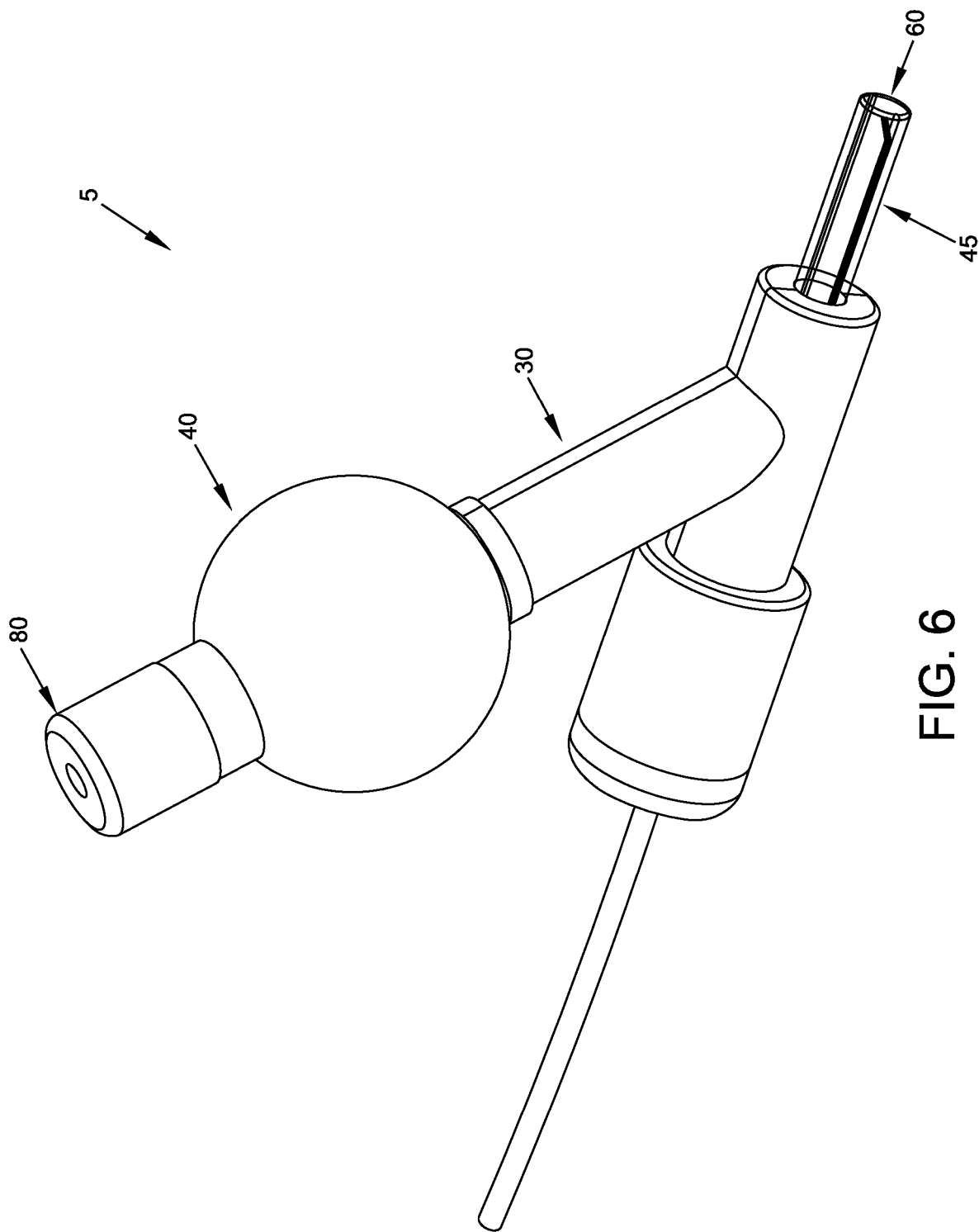
FIGS. 6-12 are schematic views showing novel apparatus formed in accordance with the present invention for evoking and sensing ophthalmic physiological signals in an eye.
Figure 7:
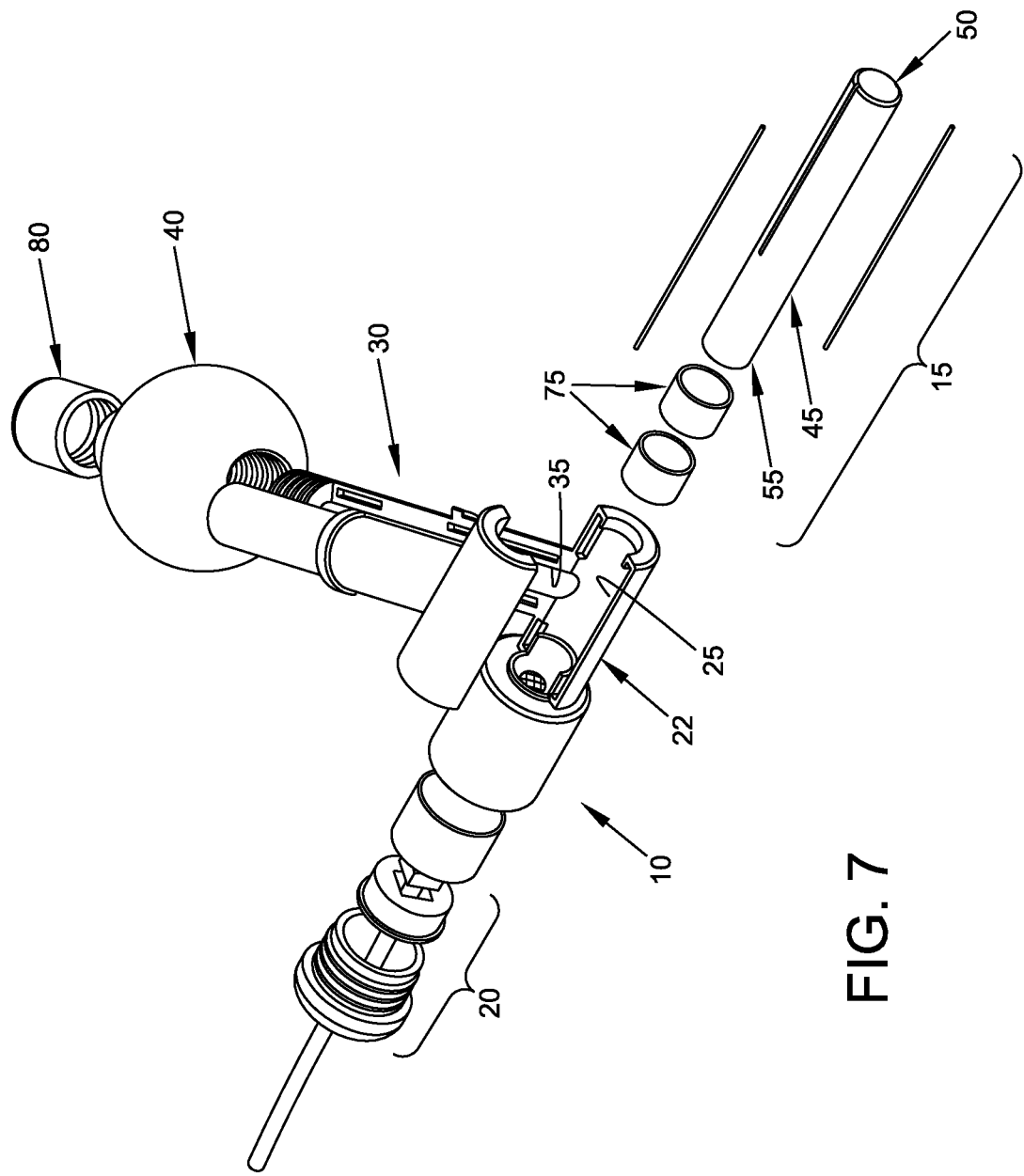
Figure 8:
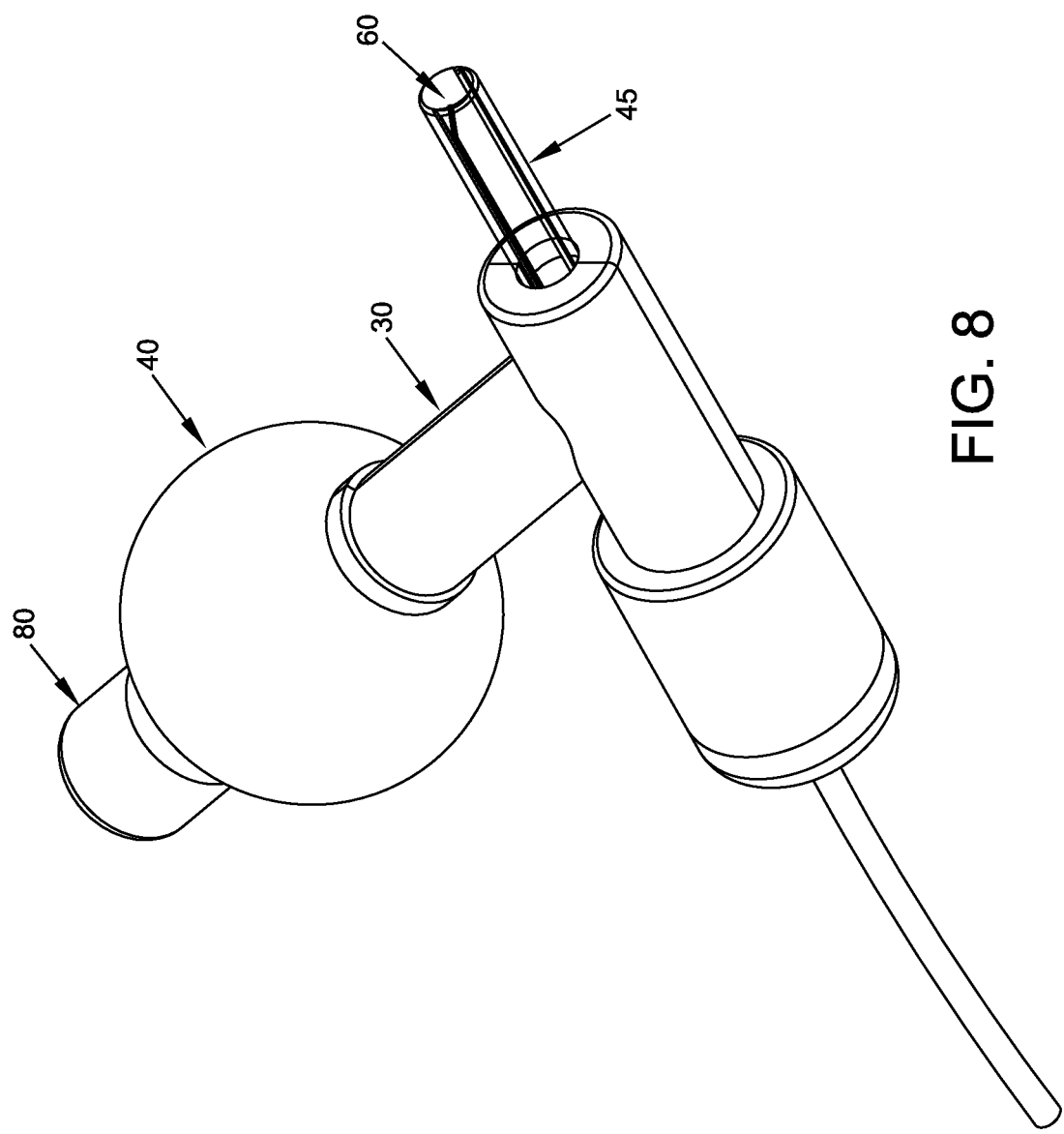
Figure 9:
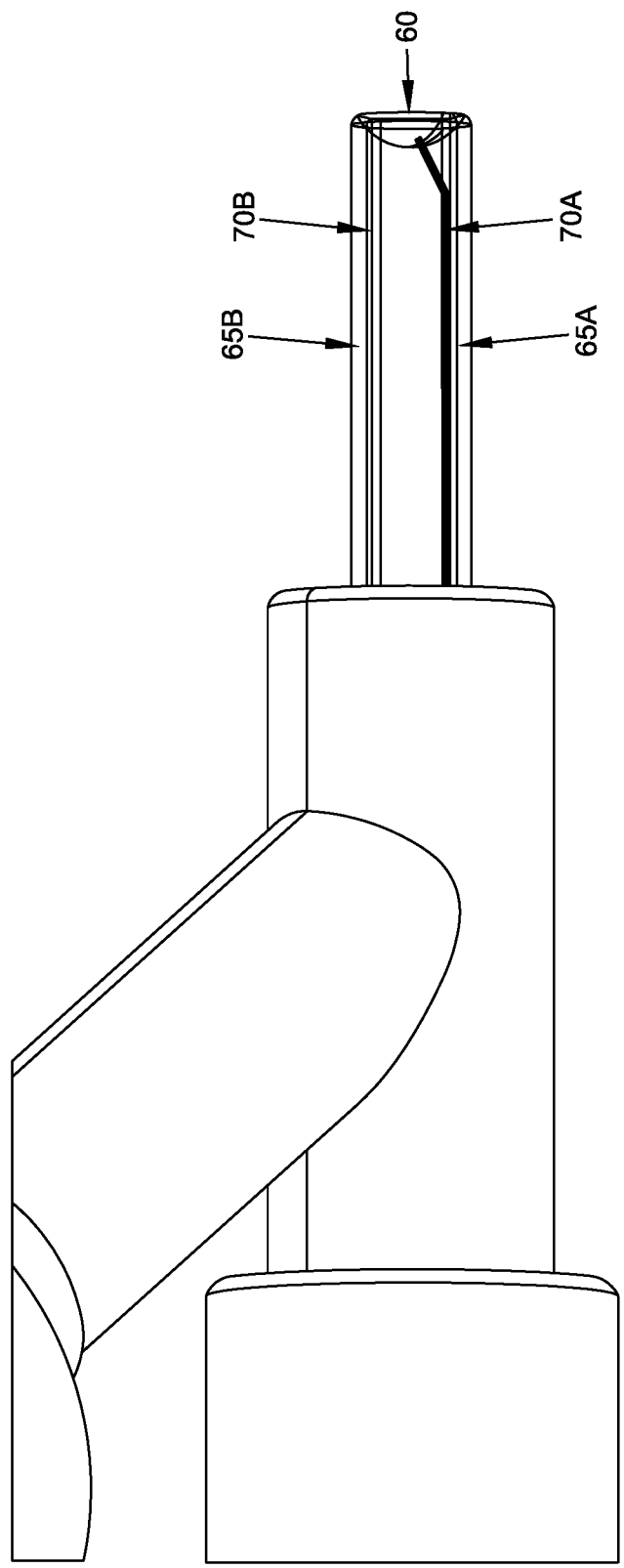
Figure 10:
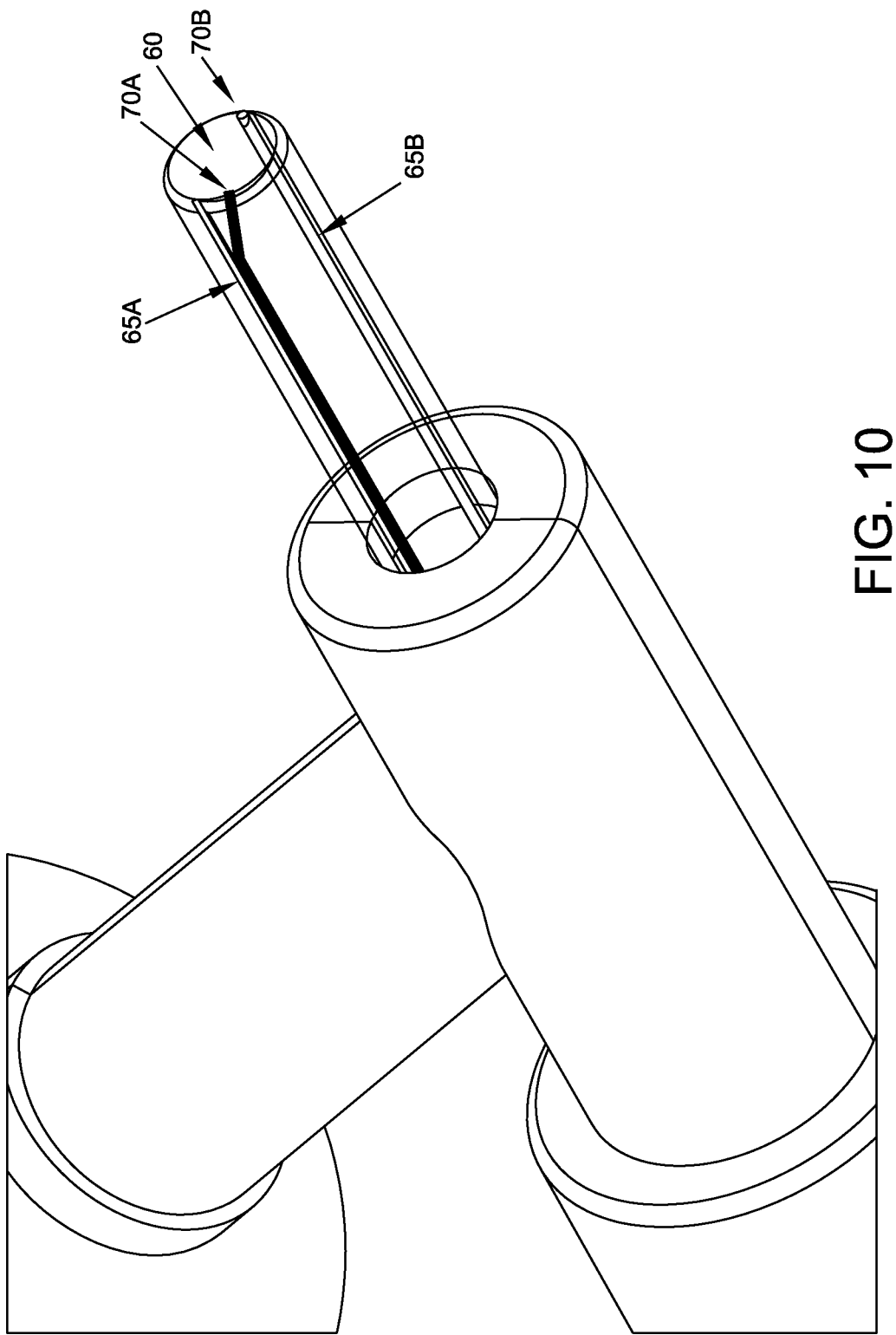
Figure 11:
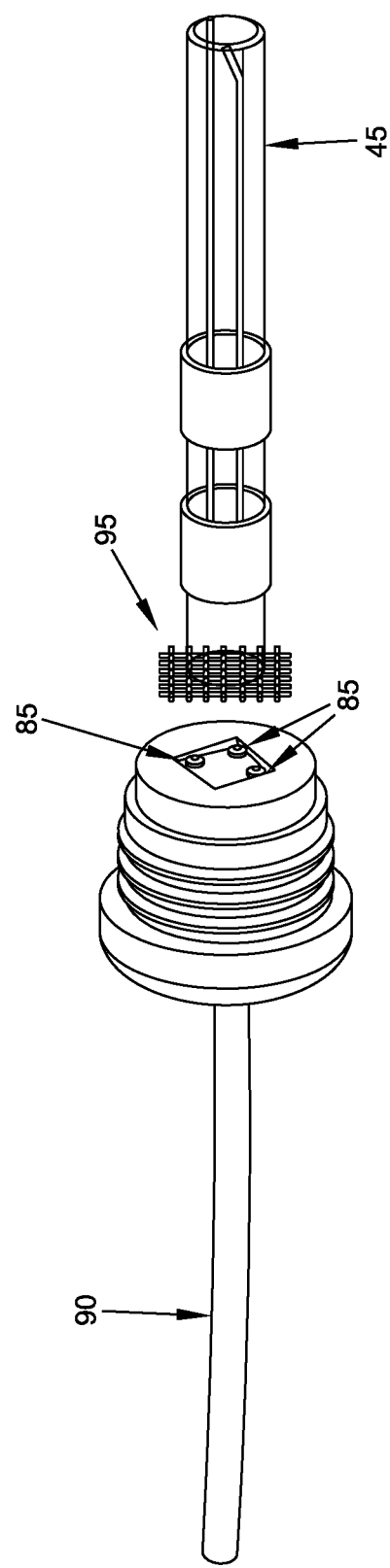

The present invention provides a new and improved approach for quickly and easily performing ophthalmic electrophysiology on mice.

More particularly, and looking now at FIGS. 6-11, there is shown a combined stimulator and bipolar electrode assembly 5 formed in accordance with the present invention. Combined stimulator and bipolar electrode assembly 5 generally comprises a housing 10, a light pipe subassembly 15 and a light source subassembly 20.

Housing 10 preferably comprises a main body 22 having a cavity 25 formed therein, and a side arm 30 extending at an angle (e.g., 125 degrees) to the longitudinal axis of main body 22. Side arm 30 includes a cavity 35 formed therein, and a magnetic mount 40 (preferably in the form of a steel ball) secured to side arm 30.

Light pipe subassembly 15 is disposed partially within, and protrudes from, cavity 25 of main body 22. Light pipe subassembly 15 generally comprises a light pipe 45 formed out of a light-transmissive material (e.g., Plexiglass) and having a distal end 50 and a proximal end 55. Light pipe 45 has an elongated configuration, and may be cylindrical (e.g., substantially straight with a substantially circular cross-section), or non-linear pseudo-cylindrical (e.g., bent or curved with a substantially circular cross-section), or light pipe 45 may have another acceptable configuration. Distal end 50 of light pipe 45 has a spheroid recess 60 formed therein. The radius of curvature of spheroid recess 60 is preferably similar to the radius of curvature of the eye of a mouse, so that the distal end 50 of light pipe 45 can be seated against the outside surface of the eye of a mouse. Light pipe 45 also comprises a pair of slots 65A, 65B formed in the outer surface of light pipe 45. In one preferred form of the invention, slots 65A, 65B are diametrically opposed to one another. The distal end of slot 65A has a greater depth than the remainder of slot 65A, so that the distal end of slot 65A approaches (but preferably does not reach) the center of spheroid recess 60. Preferably at least the distal portion of slot 65A outboard of wire 70A is filled with an appropriate material (e.g., a light-transmissive, non-conductive, water-proof material) so as to eliminate air gaps between light pipe 45 and the eye of the mouse. A platinum (or silver or gold, etc.) wire 70A, which serves as the active electrode for combined stimulator and bipolar electrode assembly 5, is disposed in slot 65A. Note that the distal end of platinum wire 70A follows the floor of slot 65A so that the distal end of platinum wire 70A approaches the center of spheroid recess 60. The distal end of platinum wire 70A communicates with spheroid recess 60. A platinum (or silver or gold, etc.) wire 70B, which serves as the reference electrode for combined stimulator and bipolar electrode assembly 5, is disposed in slot 65B. The distal end of platinum wire 70B also communicates with spheroid recess 60. Preferably at least the distal portion of slot 65B outboard of wire 70B is filled with an appropriate material (e.g., a light-transmissive, non-conductive, waterproof material) so as to eliminate air gaps between light pipe 45 and the eye of the mouse. Note that the distance between the distal end of platinum wire 70A (which will act as the active electrode) and the distal end of platinum wire 70B (which will act as the reference electrode) is substantially equal to the distance between a portion of the eye which exhibits an evoked physiological signal and a portion of the eye which exhibits a lesser evoked physiological signal (or, preferably, does not exhibit an evoked physiological signal), e.g., the distance between the cornea and the perimeter of the eye. The intermediate portions of platinum wires 70A, 70B may be held to the body of light pipe 45 with shrink bands 75. The proximal end 55 of light pipe 45 is disposed in cavity 25 of main body 20, and the proximal ends of platinum wires 70A, 70B are passed through cavity 35 of side arm 30 so that they can be brought out the proximal end 80 of side arm 30 for connection to appropriate amplification (e.g., by a differential amplifier) and processing electronics (not shown) for ERG signal processing.

Light source subassembly 20 is disposed within cavity 25 of main body 20. Light source subassembly 20 generally comprises LEDs 85 for generating light, and any appropriate optics (not shown) required to transmit the light generated by LEDs 85 into the proximal end 55 of light pipe 45, whereupon the light will travel down the length of light pipe 45 to the distal end 50 of light pipe 45. A power line 90 provides power to LEDs 85. Preferably a wire mesh 95 (or similar element) is provided distal to LEDs 85 and proximal to platinum wires 70A, 70B so as to provide electromagnetic interference (EMI) shielding between LEDs 85 and platinum wires 70A, 70B.

It will be appreciated that, on account of the foregoing construction, combined stimulator and bipolar electrode assembly 5 can be supported via its magnetic mount 40 for use with an ERG mouse platform, with the proximal ends of platinum wires 70A, 70B being connected to appropriate amplification and processing electronics for ERG signal processing, and with power line 90 being connected to an appropriate source of power. When a mouse is to be tested, the mouse is placed on the ERG mouse platform, a ground electrode (not shown) is attached to the mouse, and then housing 10 can be moved so as to bring the distal end 50 of light pipe 45 into contact with the eye of the mouse. This action will position the distal end of platinum wire 70A (i.e., the active electrode) at the appropriate position on the eye of the mouse, and will simultaneously position the distal end of platinum wire 70B (i.e., the reference electrode) at another appropriate position on the eye of the mouse. When LEDs 85 are thereafter energized, the light from LEDs 85 passes down light pipe 45 and into the eye of the mouse, whereby to stimulate the eye of the mouse. Platinum wires 70A (i.e., the active electrode) and 70B (i.e., the reference electrode) pick up the electrophysiological response of the eye of the mouse as electrical signals, and these electrical signals are passed along platinum wires 70A, 70B to appropriate amplification and processing electronics for ERG signal processing.

Thus it will be seen that with the combined stimulator and bipolar electrode assembly 5 of the present invention, the assembly simultaneously provides (i) the stimulator needed for conducting ophthalmic electrophysiology on a mouse (i.e., LEDs 85 and light pipe 45), (ii) the bipolar electrode needed for conducting ophthalmic electrophysiology on a mouse (i.e., platinum wires 70A, 70B supported by light pipe 45), and (iii) the support structure (e.g., magnetic mount 40) for holding the bipolar electrode securely against the eye during testing.

Significantly, mounting platinum wires 70A, 70B to the light pipe 45 provides a robust mechanical support for the platinum wires, making it possible to quickly, easily and precisely position the active electrode (i.e., platinum wire 70A) and the reference electrode (i.e., platinum wire 70B) on the eye of the mouse. At the same time, the small acceptance angle of light pipe 45 restricts the light reaching the eye of the mouse to that generated by LEDs 85, which eliminates the normal need for a large Ganzfeld to conduct ophthalmic electrophysiology. Note that LEDs 85 may be a three-color RGB system, although UV could also be used and would be desirable in mice. In one preferred form of the invention, appropriate electronic drivers are provided to drive RGB LEDs 85 accurately enough to form precisely-defined metameric colors.

Figure 12:
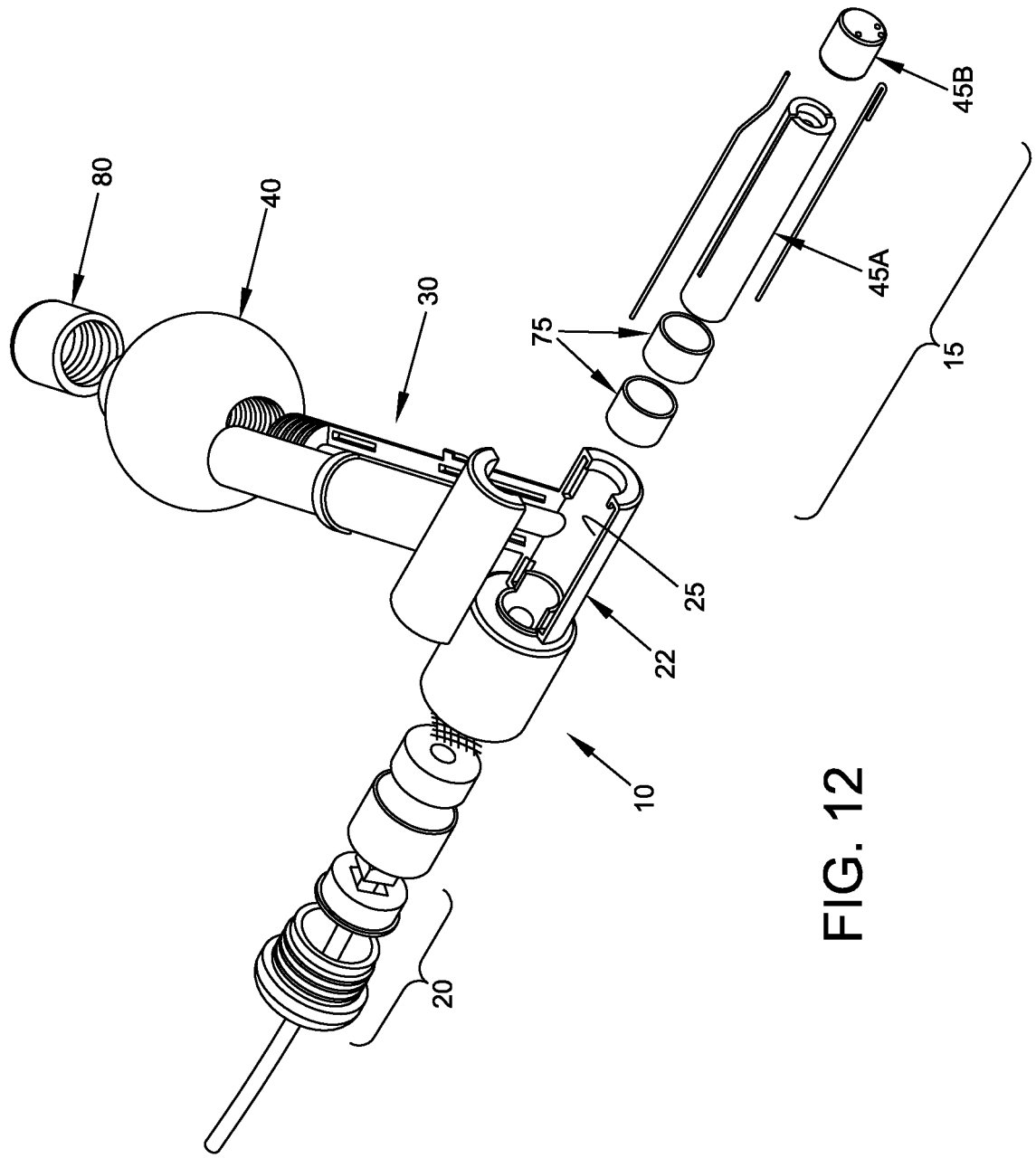
Figure 13:
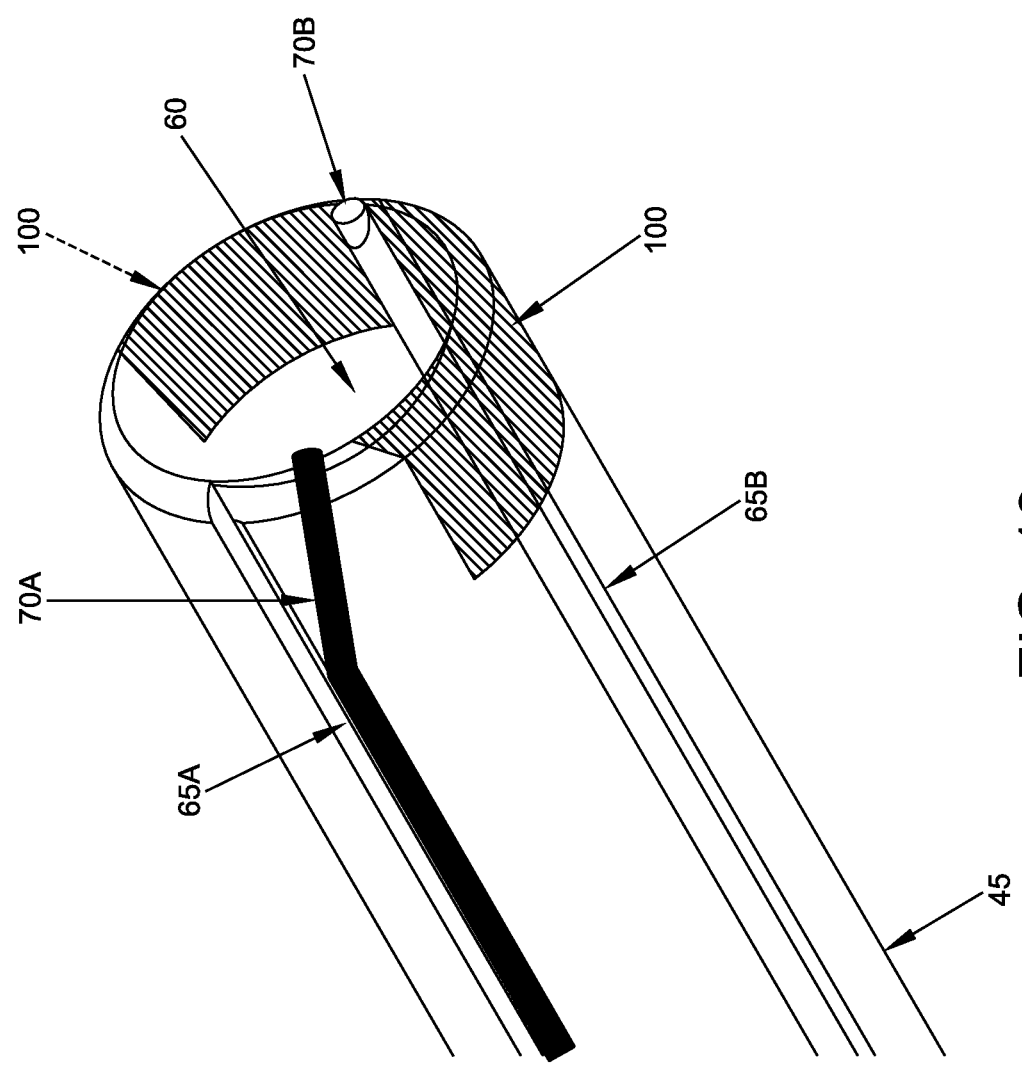
FIG. 13 is a schematic view showing an alternative form of the apparatus shown in FIGS. 6-12.

If desired, and looking now at FIG. 12, light pipe 45 may comprise a main body 45A and an end diffuser 45B. End diffuser 45B can, advantageously, help provide full retinal illumination. More particularly, end diffuser 45B acts to broaden the angle at which light exits main body 45A of light pipe 45 and enters the eye of the mouse, and ensures that light exiting the light pipe is distributed equally to all parts of the retina of the mouse. The diffusing material of end diffuser 45B is preferably of non-uniform thickness, i.e., it is made thinner at the edges to compensate for the lower flux density occurring at the perimeter of the light pipe. Furthermore, if desired, reference electrode 70B may be "doubled over" so as to increase the surface area contact of reference electrode 70B with the eye of the mouse. And, if desired, and looking now at FIG. 13, a conductive foil (or conductive film) 100 may be provided at distal end 50 of light pipe 45, with conductive foil (or conductive film) 100 electrically connected to reference electrode 70B so as to increase the surface area contact of reference electrode 70B with the eye of the mouse.

Figure 14:
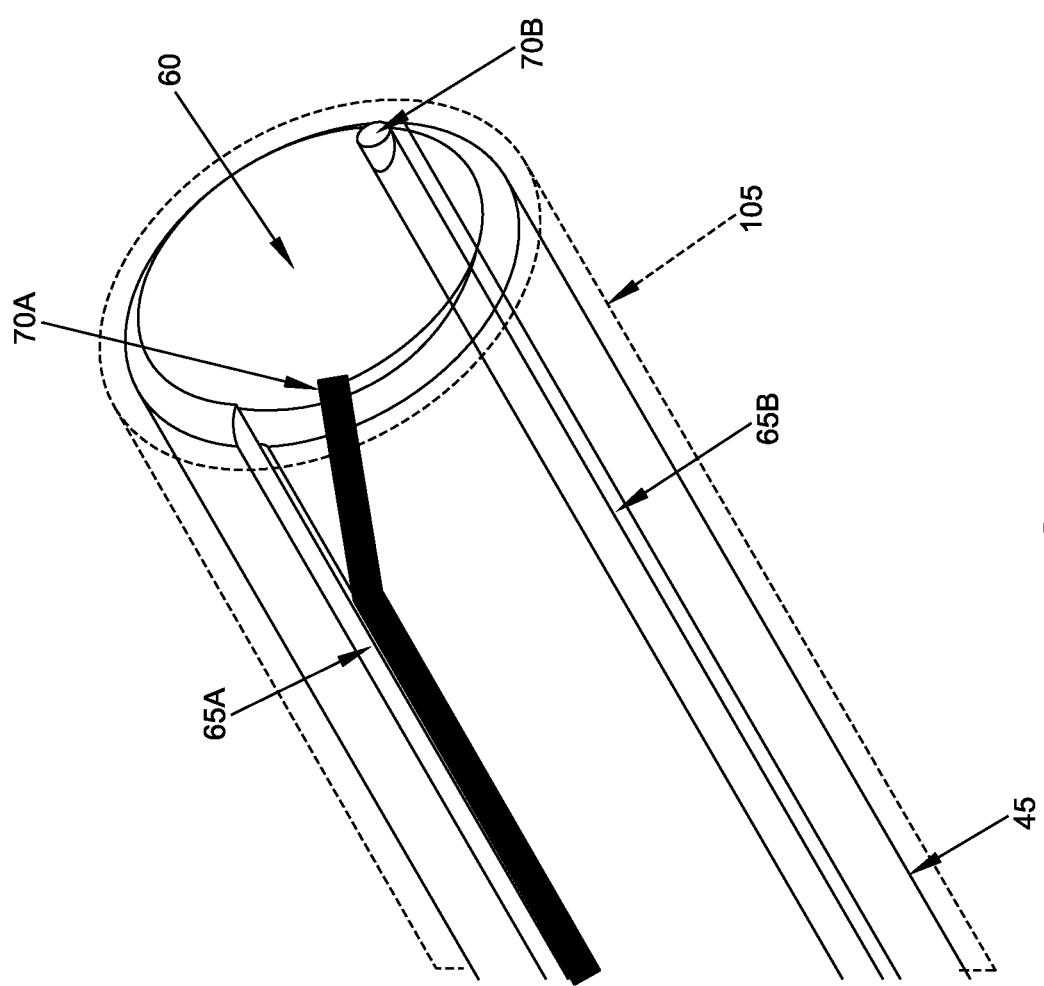
FIG. 14 is a schematic view showing another alternative form of the apparatus shown in FIGS. 6-12.

In some cases, it can be helpful to provide the user with "red light" illumination to help the user set the combined stimulator and bipolar electrode assembly 5 against the eye of the mouse. To this end, if desired, and looking now at FIG. 14, a light-transmissive sleeve 105 may be disposed coaxially about light pipe 45, with light-transmissive sleeve 105 acting as an additional light pipe for delivering red light to the distal end of light pipe 45. More particularly, in this form of the invention, when red light is introduced into the proximal end of light-transmissive sleeve 105, a ring of red light will be provided at the distal end of light-transmissive sleeve 105, whereby to provide a rim of red illuminating light about the distal perimeter of light pipe 45.

The combined stimulator and bipolar electrode assembly 5 of the present invention can be set up not only more accurately, but also much more quickly, than the present state-of-the-art, even by relatively unskilled personnel. After positioning the mouse on the heated table described above and inserting the ground electrode (e.g., in the haunch or tail of the animal), the combined stimulator and bipolar electrode assembly 5 is simply brought into contact with the eye of the mouse by moving housing 10 (which causes magnetic mount 40, e.g., a steel ball), to roll within a magnetic cup, e.g., a magnetic ball holder (see FIG. 1 above, which shows a magnetic ball holder of the sort which may be used), and then the test is ready to run. A second device can be used simultaneously on the fellow eye (i.e., the other eye of the mouse) if desired. This eliminates several minutes fumbling in near darkness to carefully adjust the electrodes and position the Ganzfeld. Additionally, since light pipe subassembly 15 is held in position against the eye by an external mechanical mount (i.e., magnetic mount 40) and is not supported by the eye per se, it is not necessary to use particular care to position combined stimulator and bipolar electrode assembly 5 precisely against structurally robust eye tissue. Furthermore, since light pipe subassembly 15 has no accessible distal surface once it is seated against the eye, it is substantially impossible to obscure the light path from light pipe subassembly 15 into the eye by the use of excessive saline.

Testing of the combined stimulator and bipolar electrode assembly 5 on mice has yielded excellent results. It produces expected waveforms with very little noise, although the overall amplitude of the waveforms is small.

In addition to the foregoing, some investigators have used an active electrode in one eye, and a reference electrode in the other eye. This technique still involves accurate placement of two corneal wires (extremely challenging with prior art electrodes), but the fellow eye makes an excellent impedance-matched reference. However, with this approach, care must be taken to avoid light crosstalk between the eyes—the reference eye must not receive any stimulus light.

Using the combined stimulator and bipolar electrode assembly 5 of the present invention solves both problems (i.e., accurate placement of electrode and avoiding light crosstalk between the eyes). More particularly, in one form of the invention, the corneal electrode 70A of, for example, the right eye is plugged into the active side of the differential amplifier, and the corneal electrode 70A of the left eye into the reference side of the differential amplifier. The electrodes in each eye are automatically correctly positioned. The eyes are then stimulated one at a time using the light source subassemblies 20 of the combined stimulator and bipolar electrode assemblies 5, and there is no optical crosstalk because of the light pipe configuration (i.e., the positioning of a light pipe on an eye of the mouse limits the light reaching that eye of the mouse to only the light transmitted by that light pipe). When the right eye is being driven, the signal is normally polarized, and when the left eye is being driven, the signal is inverted. Alternatively, both eyes of the mouse could be simultaneously stimulated using light source subassemblies 20 of the combined stimulator and bipolar electrode assemblies 5, and the differential between the two corneal electrodes 70A may be measured so as to identify differences in eye function.

Alternatively, the reference electrodes 70B may be used in place of the corneal electrodes 70A. In this form of the invention, the reference electrode 70B of, for example, the right eye is plugged into the active side of the differential amplifier, and the reference electrode 70B of the left eye is plugged into the reference side of the differential amplifier. The electrodes in each eye are automatically correctly positioned. The eyes are then stimulated one at a time using the light source subassemblies 20 of the combined stimulator and bipolar electrode assemblies 5, and there is no optical crosstalk because of the light pipe configuration (i.e., the positioning of a light pipe on an eye of the mouse limits the light reaching that eye of the mouse to only the light transmitted by that light pipe). When the right eye is being driven, the signal is correctly polarized, and when the left eye is being driven, the signal is inverted. Alternatively, both eyes of the mouse may be simultaneously stimulated using light source subassemblies 20 of the combined stimulator and bipolar electrode assemblies 5, and the differential between the two reference electrodes 70B may be measured so as to identify differences in eye function.

Figure 15:
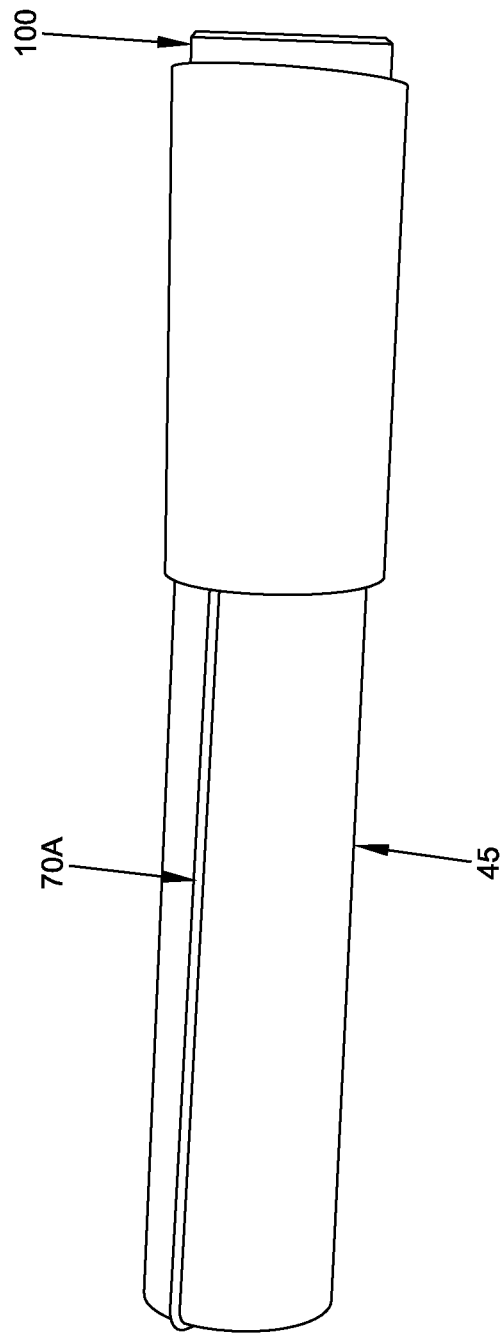
FIGS. 15-17 are schematic views showing exemplary novel apparatus formed in accordance with the present invention for evoking and sensing ophthalmic physiological signals in an eye.
Figure 16:
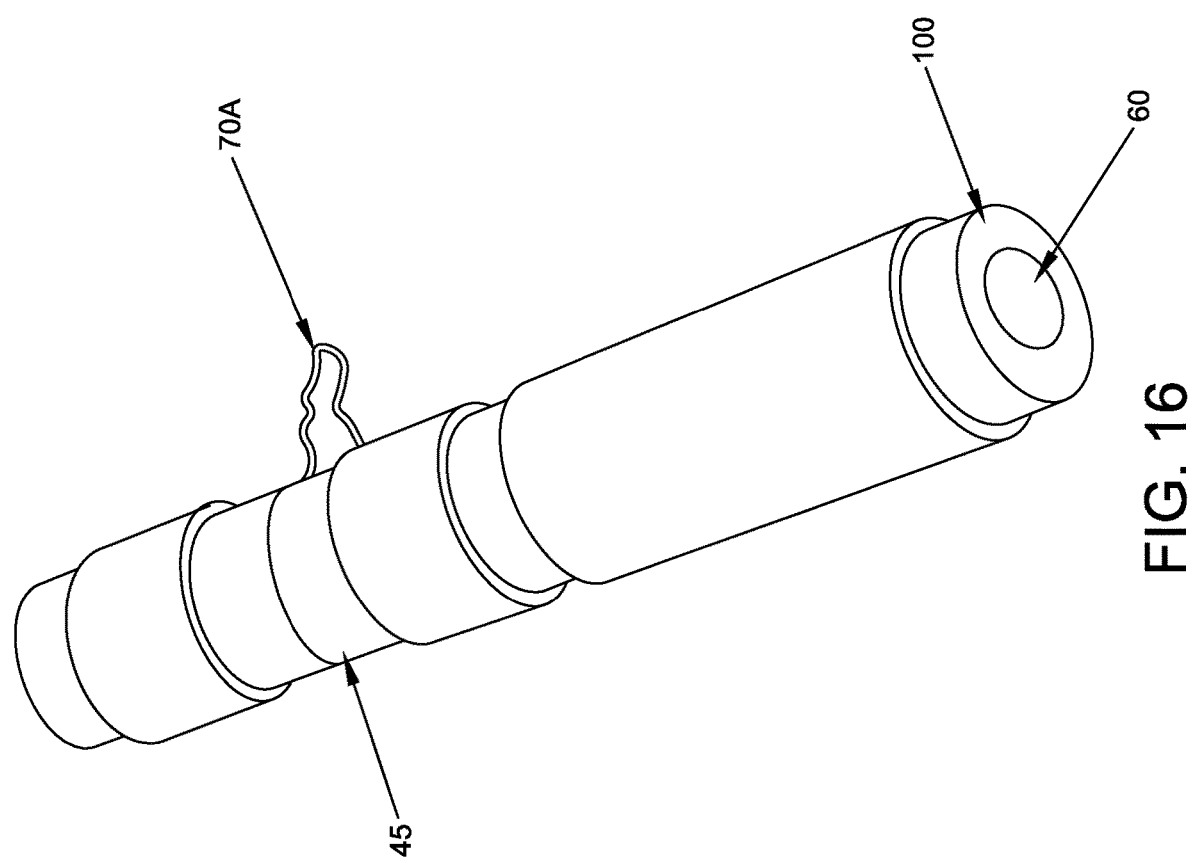
Figure 17:
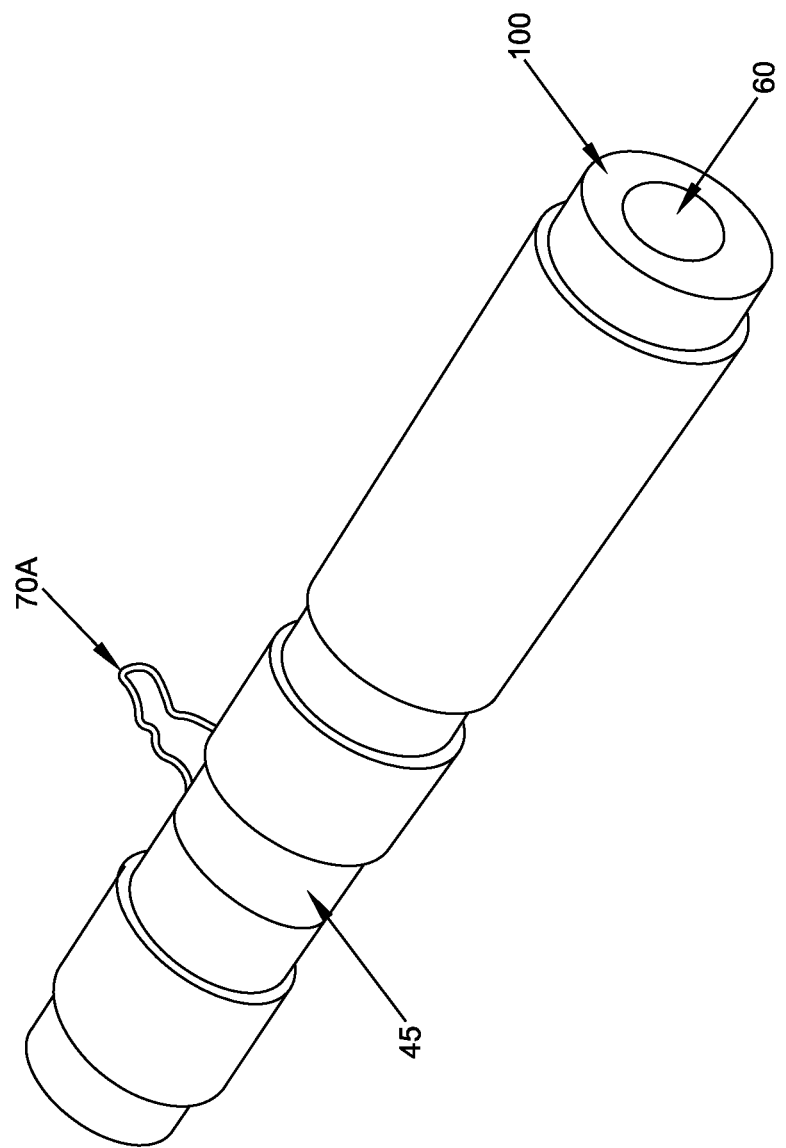

In one preferred form of the invention, and looking now at FIGS. 15-17, platinum wire 70A can be omitted and platinum wire 70B can be provided with a conductive foil (or conductive film) 100. When configured in this manner, the present invention essentially comprises a combined stimulator and monopolar electrode assembly. This form of the invention can be advantageous where combined stimulator and monopolar electrode assemblies are positioned against both eyes of the mouse (for stimulating one eye at a time or for simultaneously stimulating both eyes at the same time).

The robustness of the electrical and optical connections that the new combined stimulator and bipolar electrode assembly 5 makes with the mouse has been dramatically demonstrated during testing. Toward the end of testing, the mice may wake up and begin to move. With conventional setups, the first movement of the awakening mouse breaks corneal contact and the testing is over. With the combined stimulator and bipolar electrode assembly 5 of the present invention, contact with the awakening mouse was successfully maintained even though the mouse was moving and testing continued with good results until the mouse literally walked away.

In the foregoing disclosure, platinum wire 70A (i.e., the active electrode) is disposed within slot 65A which extends along an outer surface of light pipe 45, and platinum wire 70B (i.e., the reference electrode) is disposed within slot 65B which extends along an outer surface of light pipe 45. However, if desired, slot 65A could be replaced with a bore extending longitudinally through light pipe 45 and platinum wire 70A (i.e., the active electrode) may be disposed within this longitudinal bore, and/or slot 65B could be replaced with another bore extending longitudinally through light pipe 45 and platinum wire 70B (i.e., the reference electrode) may be disposed within this other longitudinal bore. In such a construction, the longitudinal bore receiving platinum wire 70A (i.e., the active electrode) is disposed closer to the longitudinal axis of light pipe 45 than the longitudinal bore receiving platinum wire 70B (i.e., the reference electrode).

MODIFICATIONS OF THE PREFERRED EMBODIMENTS

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. An apparatus for evoking and sensing ophthalmic physiological signals in an eye, the apparatus comprising:
   a first combined stimulator and electrode assembly, the first combined stimulator and electrode assembly comprising:
      a first elongated light transmission element having a first distal end and a first proximal end, the first distal end terminating in a first spheroid recess set within the first distal end of the first elongated light transmission element;
      a first light source for introducing light into the first elongated light transmission element so that the light from the first light source exits from the first spheroid recess, the first elongated light transmission element being constructed so that when the first elongated light transmission element is engaged with a first eye of a test subject, it optically isolates the first eye from any light other than the light from the first light source; and
      a first electrode having a first distal end and a first proximal end, the first electrode being mounted to the first elongated light transmission element so that the first distal end of the first electrode terminates at the first spheroid recess at the first distal end of the first elongated light transmission element, such that when the first elongated light transmission element is engaged with the first eye, the first electrode directly contacts the first eye; and
   a second combined stimulator and electrode assembly, the second combined stimulator and electrode assembly comprising:
      a second elongated light transmission element having a second distal end and a second proximal end, the second distal end terminating in a second spheroid recess set within the second distal end of the second elongated light transmission element;
      a second light source for introducing light into the second elongated light transmission element so that the light from the second light source exits from the second spheroid recess, the second elongated light transmission element being constructed so that when the second elongated light transmission element is engaged with a second eye of the test subject, it optically isolates the second eye from any light other than the light from the second light source; and
      a second electrode having a second distal end and a second proximal end, the second electrode being mounted to the second elongated light transmission element so that the second distal end of the second electrode terminates at the second spheroid recess at the second distal end of the second elongated light transmission element, such that when the second elongated light transmission element is engaged with the second eye, the second electrode directly contacts the second eye; and
   wherein the first combined stimulator and electrode assembly is configured to be placed in contact with the first eye of the test subject and the second combined stimulator and electrode assembly is configured to be placed in contact with the second eye of the test subject, such that when the first light source is used to stimulate the first eye of the test subject, the first electrode can serve as an active electrode and the second electrode can serve as a reference electrode to detect ophthalmic physiologic signals in the first eye.

2. Apparatus according to claim 1 wherein the first elongated light transmission element and the second elongated light transmission element comprise a configuration selected from the group consisting of cylindrical and non-linear pseudo-cylindrical.

3. Apparatus according to claim 1 wherein the first spheroid recess and the second spheroid recess are adapted to match the first and second eyes, respectfully of the test subject, wherein the test subject is a rodent.

4. Apparatus according to claim 1 wherein the first elongated light transmission element comprises a first longitudinal axis extending between the first distal end and the first proximal end of the first elongated light transmission element, and the second elongated light transmission element comprises a second longitudinal axis extending between the second distal end and the second proximal end of the second elongated light transmission element, and further wherein the first elongated light transmission element and the second elongated light transmission element comprise a light-transmissive material which only allows light passing along the first longitudinal axis to exit from the first spheroid recess, and only allows light passing along the second longitudinal axis to exit from the second spheroid recess.

5. Apparatus according to claim 4 wherein the first elongated light transmission element and the second elongated light transmission element comprise plexiglass.

6. Apparatus according to claim 1 wherein the first distal end of the first elongated light transmission element and the second distal end of the second elongated light transmission element comprise a light diffuser.

7. Apparatus according to claim 1 wherein the first electrode and the second electrode are formed out of at least one from the group consisting of platinum, silver and gold.

8. Apparatus according to claim 1 wherein the first light source and the second light source are adapted to emit light configured to evoke ophthalmic physiological signals in the first eye.

9. Apparatus according to claim 8 wherein the first light source and the second light source comprise LEDs.

10. Apparatus according to claim 9 wherein the LEDs comprise at least one red or ultraviolet LED, at least one green LED and at least one blue LED.

11. Apparatus according to claim 1 wherein the first combined stimulator and electrode assembly and the second combined stimulator and electrode assembly further comprise an electromagnetic interference (EMI) shield.

12. Apparatus according to claim 11 wherein the electromagnetic interference (EMI) shield comprises a wire mesh.

13. Apparatus according to claim 1 further comprising a first adjustable mount for supporting the first elongated light transmission element and a second adjustable mount for supporting the second elongated light transmission element.

14. Apparatus according to claim 13 wherein the first adjustable mount and the second adjustable mount comprise a magnetic ball mount.

15. Apparatus according to claim 1 wherein the first electrode provides one input to a differential amplifier, and the second electrode provides a second input to the differential amplifier.

16. Apparatus according to claim 1 wherein the first combined stimulator and electrode assembly further comprises a first additional electrode, and the second combined stimulator and electrode assembly further comprises a second additional electrode.

17. Apparatus according to claim 16 wherein the first additional electrode has a first distal end and a first proximal end, the first additional electrode being mounted to the first elongated light transmission element so that the first distal end of the first additional electrode terminates at the first spheroid recess at the first distal end of the first elongated light transmission element, and the second additional electrode has a second distal end and a second proximal end, the second additional electrode being mounted to the second elongated light transmission element so that the second distal end of the second additional electrode terminates at the second spheroid recess at the second distal end of the second elongated light transmission element.

18. A method for evoking and sensing ophthalmic physiological signals in an eye, the method comprising:
providing apparatus comprising:
a first combined stimulator and electrode assembly, the first combined stimulator and electrode assembly comprising:
a first elongated light transmission element having a first distal end and a first proximal end, the first distal end terminating in a first spheroid recess set within the first distal end of the first elongated light transmission element;
a first light source for introducing light into the first elongated light transmission element so that the light from the first light source exits from the first spheroid recess, the first elongated light transmission element being constructed so that when the first elongated light transmission element is engaged with a first eye of a test subject, it optically isolates the first eye from any light other than the light from the first light source; and
a first electrode having a first distal end and a first proximal end, the first electrode being mounted to the first elongated light transmission element so that the first distal end of the first electrode terminates at the first spheroid recess at the first distal end of the first elongated light transmission element, such that when the first elongated light transmission element is engaged with the first eye, the first electrode directly contacts the first eye; and
a second combined stimulator and electrode assembly, the second combined stimulator and electrode assembly comprising:
a second elongated light transmission element having a second distal end and a second proximal end, the second distal end terminating in a second spheroid recess set within the second distal end of the second elongated light transmission element;
a second light source for introducing light into the second elongated light transmission element so that the light from the second light source exits from the second spheroid recess, the second elongated light transmission element being constructed so that when the second elongated light transmission element is engaged with a second eye of the test subject, it optically isolates the second eye from any light other than the light from the second light source; and
a second electrode having a second distal end and a second proximal end, the second electrode being mounted to the second elongated light transmission element so that the second distal end of the second electrode terminates at the second spheroid recess at the second distal end of the second elongated light transmission element, such that when the second elongated light transmission element is engaged with the second eye, the second electrode directly contacts the second eye;
positioning the first elongated light transmission element against the first eye of the test subject;
positioning the second elongated light transmission element against the second eye of the test subject;
introducing light into the proximal end of the first elongated light transmission element so that the light from the first light source exits from the first spheroid recess to stimulate the first eye of the test subject; and
using the first electrode as an active electrode and using the second electrode as a reference electrode to detect ophthalmic physiologic signals in the first eye of the test subject.

19. A method according to claim 18 wherein the first spheroid recess and the second spheroid recess are adapted to match the first and second eyes, respectfully of the test subject, wherein the test subject is a rodent.

20. A method according to claim 18 wherein the first electrode and the second electrode are formed out of at least one from the group consisting of platinum, silver and gold.

21. A method according to claim 18 wherein the first light source and the second light source are adapted to emit light configured to evoke ophthalmic physiological signals in the first eye.

22. A method according to claim 21 wherein the first light source and the second light source comprise LEDs.

23. A method according to claim 22 wherein the LEDs comprise at least one red or ultraviolet LED, at least one green LED and at least one blue LED.

24. A method according to claim 18 further comprising a first adjustable mount for supporting the first elongated light transmission element and a second adjustable mount for supporting the second elongated light transmission element.

25. A method according to claim 24 wherein the first adjustable mount and the second adjustable mount comprise a magnetic ball mount.

26. A method according to claim 18 wherein the first electrode provides one input to a differential amplifier, and the second electrode provides a second input to the differential amplifier.

27. A method according to claim 18 wherein the first combined stimulator and electrode assembly further comprises a first additional electrode, and the second combined stimulator and electrode assembly further comprises a second additional electrode.

28. A method according to claim 27 wherein the first additional electrode has a first distal end and a first proximal end, the first additional electrode being mounted to the first elongated light transmission element so that the first distal end of the first additional electrode terminates at the first spheroid recess at the first distal end of the first elongated light transmission element, and the second additional electrode has a second distal end and a second proximal end, the second additional electrode being mounted to the second elongated light transmission element so that the second distal end of the second additional electrode terminates at the second spheroid recess at the second distal end of the second elongated light transmission element.

29. Apparatus for evoking and sensing ophthalmic physiological signals in an eye, the apparatus comprising:
an elongated tubular light pipe having a longitudinal axis, a distal end and a proximal end, the distal end terminating in a spheroid recess;
an active electrode having a distal end and a proximal end, the active electrode being mounted to the elongated tubular light pipe and extending proximally along the elongated tubular light pipe so that the distal end of the active electrode terminates at the spheroid recess at the distal end of the elongated tubular light pipe; and
a reference electrode having a distal end and a proximal end, the reference electrode being mounted to the elongated tubular light pipe and extending proximally along the elongated tubular light pipe so that the distal end of the reference electrode terminates at the spheroid recess at the distal end of the elongated tubular light pipe;
wherein the distal end of the active electrode is located closer to the longitudinal axis of the elongated tubular light pipe than the distal end of the reference electrode;
wherein the elongated tubular light pipe comprises a first slot and a second slot, and further wherein the active electrode is disposed at least partially in the first slot and the reference electrode in disposed at least partially in the second slot.

30. Apparatus according to claim 29 wherein the first slot comprises a distal end and a proximal end, the second slot comprises a distal end and a proximal end, and further wherein the distal end of the first slot is located closer to the longitudinal axis of the elongated tubular light pipe than the distal end of the second slot.

31. Apparatus according to claim 29 wherein the first slot comprises a first straight section and a second straight section, wherein the second straight section is disposed distal to the first straight section, and further wherein the second straight section is angled relative to the first straight section.

* * * * *